United States Patent
Kim et al.

(10) Patent No.: US 8,143,384 B2
(45) Date of Patent: Mar. 27, 2012

(54) MUTATION OF PRPS1 GENE CAUSING CMTX5 DISEASE AND THE USE THEREOF

(75) Inventors: Jong Won Kim, Seoul (KR); Hee Jin Kim, Seoul (KR)

(73) Assignee: Sungkyunkwan University Foundation for Corporate Collaboration, Gyeonggi-Do (KR)

( * ) Notice: Subject to any disclaimer, the term of this patent is extended or adjusted under 35 U.S.C. 154(b) by 497 days.

(21) Appl. No.: 12/227,980

(22) PCT Filed: Dec. 28, 2007

(86) PCT No.: PCT/KR2007/006994
§ 371 (c)(1),
(2), (4) Date: Dec. 4, 2008

(87) PCT Pub. No.: WO2009/084753
PCT Pub. Date: Jul. 9, 2009

(65) Prior Publication Data
US 2010/0304365 A1    Dec. 2, 2010

(51) Int. Cl.
*C07H 21/04* (2006.01)
*C07H 21/02* (2006.01)
*C12P 19/34* (2006.01)
*C12Q 1/68* (2006.01)

(52) U.S. Cl. .............. 536/23.5; 536/24.3; 536/24.1; 435/91.2; 435/6

(58) Field of Classification Search .............. None
See application file for complete search history.

(56) References Cited

U.S. PATENT DOCUMENTS

| | | | | |
|---|---|---|---|---|
| 6,582,908 B2 * | 6/2003 | Fodor et al. | | 506/9 |
| 6,812,339 B1 * | 11/2004 | Venter et al. | | 536/24.31 |
| 2005/0085436 A1 * | 4/2005 | Li et al. | | 514/44 |

OTHER PUBLICATIONS

Brouwer et al. (The American Journal of Human Genetics Sep. 2007 vol. 81 p. 508).*
Brouwer et al. (The American Journal of Human Genetics 2010 vol. 86 p. 50).*
Hee-Jin Kim et al., "Mutations in *PRPS1*, which Encodes the Phosphoribosyl Pyrophosphate Synthetase Enzyme Critical for Nucleotide Biosynthesis, Cause Hereditary Peripheral Neuropathy with Hearing Loss and Optic Neuropahty (CMTX5)", *Am. J. of Human Gen.*, vol. 81, pp. 552-558 (Sep. 2007).
H. Skre, "Genetic and clinical aspects of Charcot-Marie-Tooth's disease", *Clin. Gen.* vol. 6, pp. 98-118 (1974).
Roger N. Rosenberg et al., "Familial Opticoacoustic nerve degeneration and polyneuropathy", *Neurology*, vol. 17. No. 9, pp. 827-832 (Sep. 1967).
J. Bergoffen et al., "Connexin Mutations in X-Linked Charcot-Marie-Tooth Disease", *Science*, vol. 262, pp. 2039-2042 (Dec. 24, 1993).
H-J. Kim et al., "A novel locus for X-linked recessive CMT with deafness and optic neuropathy maps to Xq21.32-q24", *Neurology*, vol. 64 pp. 1964-1967 (2005).
Barbara Resendes et al., "Gene Discovery in the Auditory System: Characterization of Additional Cochlear-Expressed Sequences", *JARO*, vol. 3, pp. 45-53 (2001).
Michael A. Becker et al., "The Genetic and Functional Basis of Purine Nucleotide Feedback-resistant Phosphoribosylpyrophosphate Synthetase Superactivity", *J. Clin. Invest.*, vol. 96, pp. 2133-2141 (Nov. 1995).
Michael A. Becker et al., "Overexpression of the Normal Phosphoribosylpyrophosphate Synthetase 1 Isoform Underlies Catalytic Superactivity of Human Phosphoribosylpyrophosphate Synthetase", *J. Biol. Chem.*, vol. 271, No. 33, pp. 19894-19899 (1996).
H.A. Simmonds et al., "An Inborn Error of Purine Metabolism, Deafness and Neurodevelopmental Abnormaility", *Hosp. for Sick Children*, (1984).
Tine A. Eriksen et al., "Structural basis for the function of *Bacillus subtilis* Phosphoribosyl-pyrophosphate synthetase", *Nature Struct. Biol.*, vol. 7, No. 4. pp. 303-308 (Apr. 2000).
Amanda C. Peltier et al. "Advances in Understanding Drug-Induced Neuropathies", *Drug Safety*, vol. 29, No. 1, pp. 23-30 (2006).
Johee K. Sul et al., "Neurologic Complications of Cancer Chemotherapy", *Sem. In Oncology*, vol. 33, pp. 324-332 (2006).
Frederick H. Hausheer et al., "Diagnosis, Management, and Evaluation of Chemotherapy-Induced Peripheral Neuropathy", , *Sem. In Oncology*, vol. 33, pp. 15-49 (2006).
Ryan R. Brinkman et al., "Human monogenic disorders—a source of novel drug targets", *Nature Reviews/Genetics*, vol. 7, pp. 249-260, (Apr. 2006).

* cited by examiner

*Primary Examiner* — Katherine Salmon
(74) *Attorney, Agent, or Firm* — Harness, Dickey & Pierce, PLC

(57) ABSTRACT

Disclosed is a gene mutation associated with peripheral neuropathy associated with sensorineural hearing loss and optic neuropathy. More specifically, disclosed are: a polynucleotide comprising a mutation associated with peripheral neuropathy associated with sensorineural hearing loss and optic neuropathy, or a complementary polynucleotide thereof; a polynucleotide which hybridizes with said polynucleotide; a polypeptide which is encoded by said polynucleotide; an antibody which binds to said polypeptide; and a microarray chip and a kit, which comprise said polynucleotide. Also disclosed are a method for diagnosing a syndrome of peripheral neuropathy associated with sensorineural hearing loss and optic neuropathy, a method for detecting the mutation, and a method for screening drugs for treating these diseases.

2 Claims, 11 Drawing Sheets

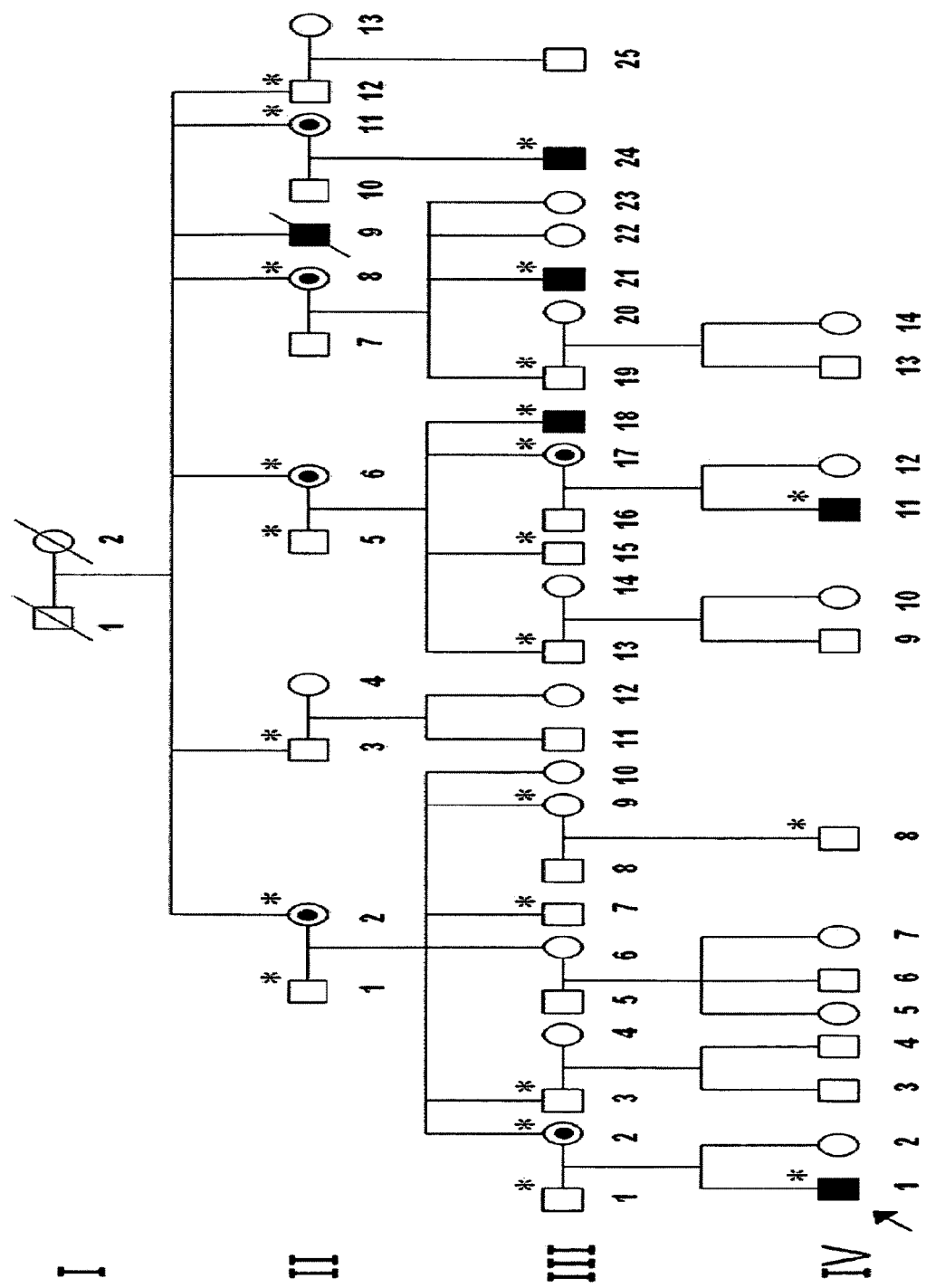
[Figure 1]

[Figure 2]
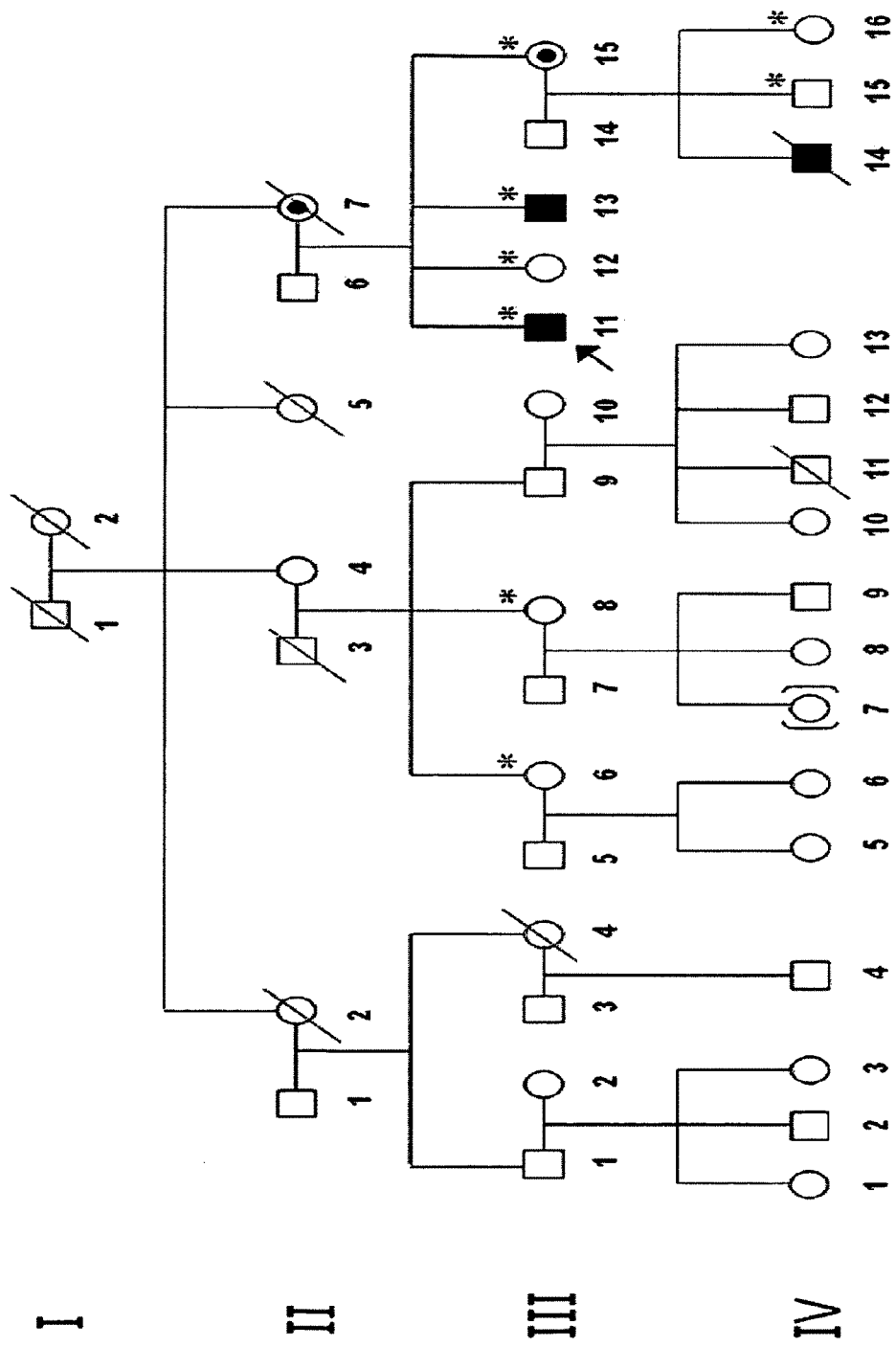

[Figure 3]
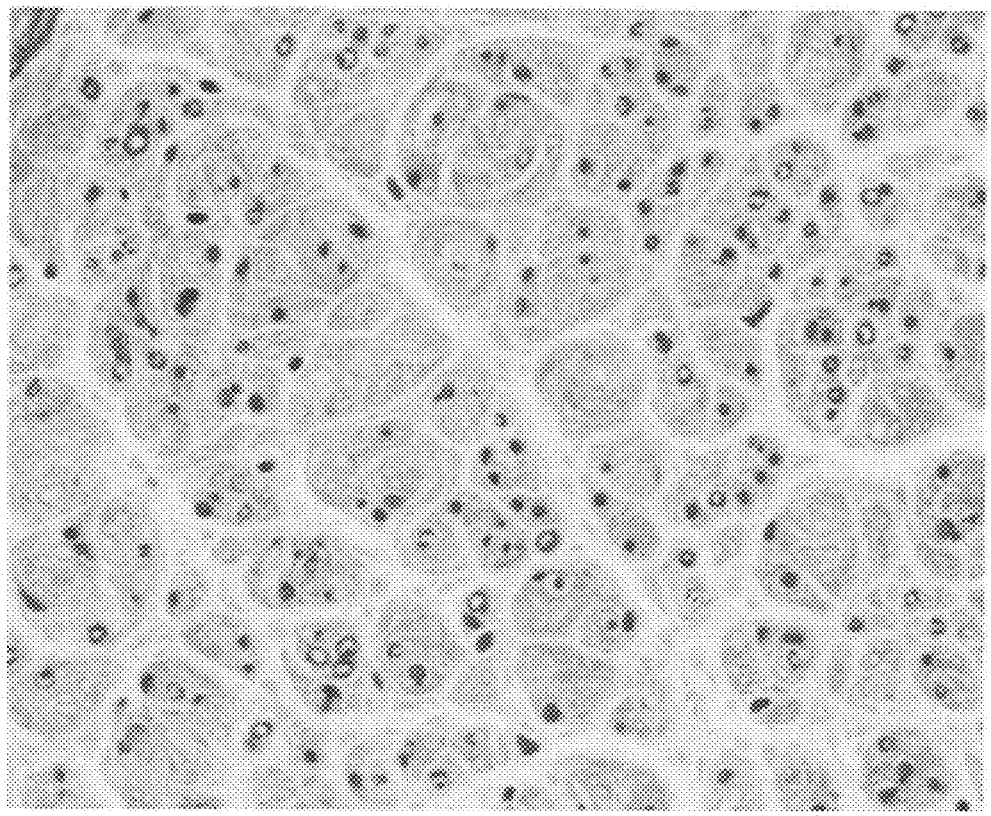

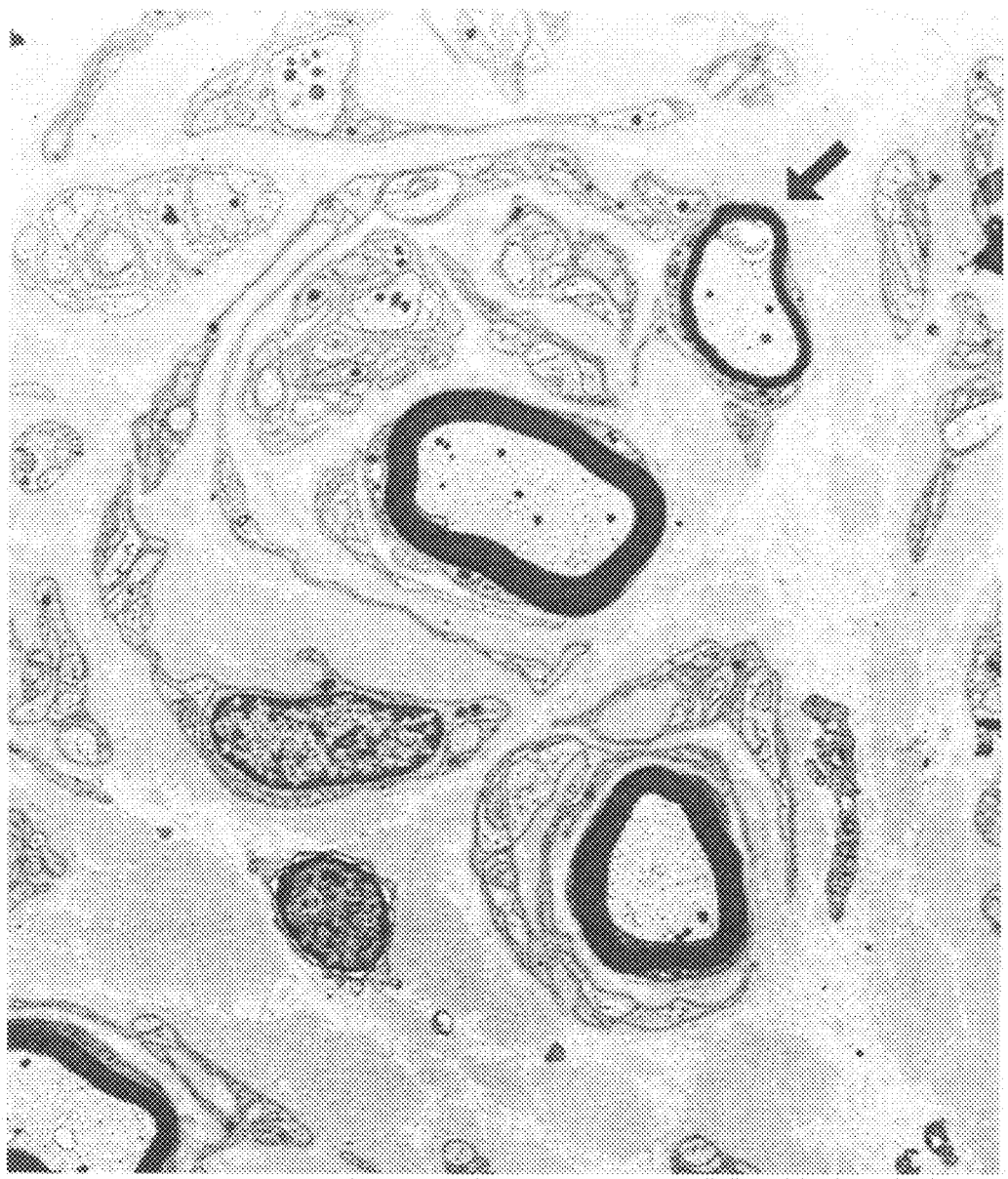
[Figure 4]

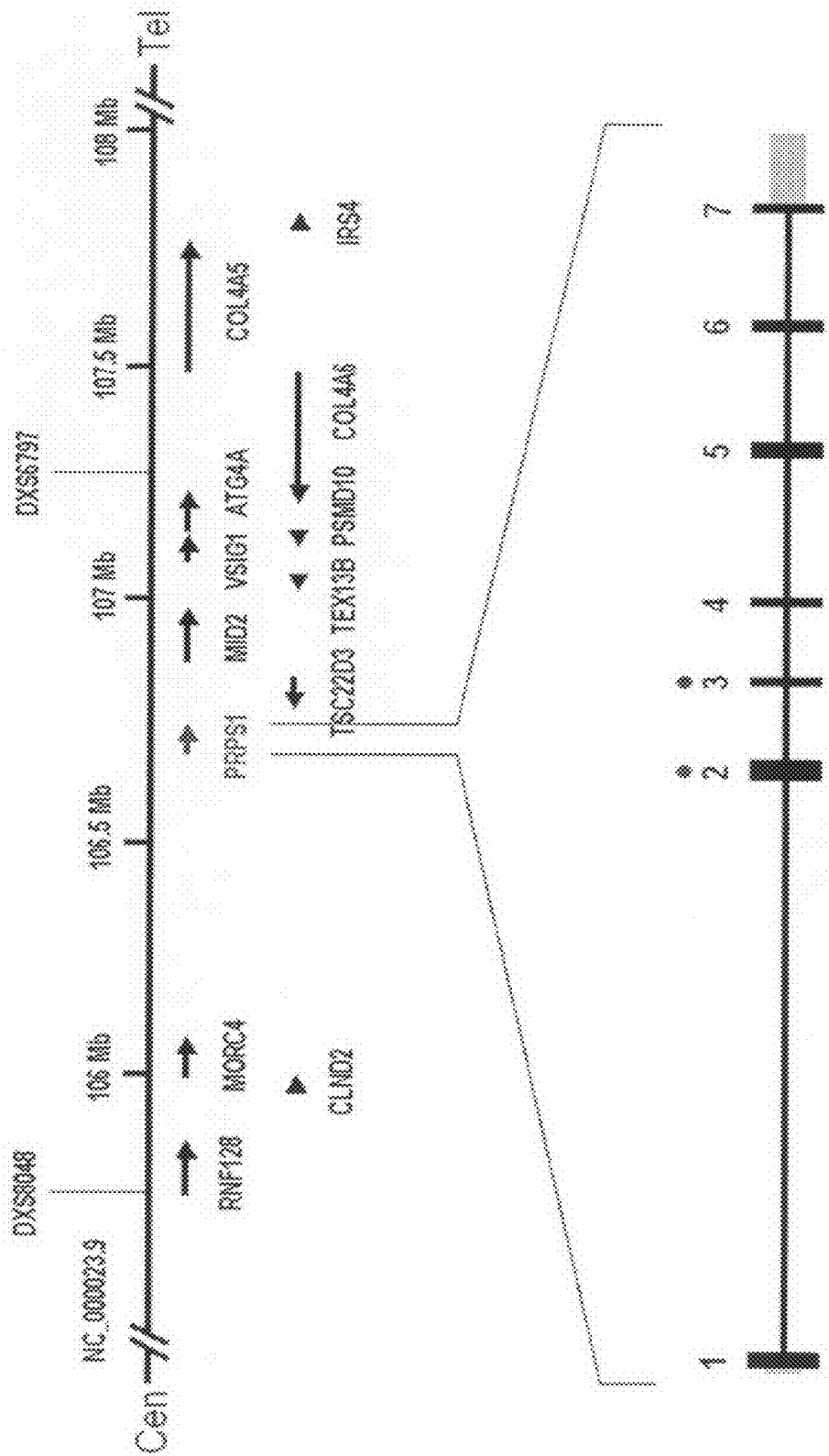
[Figure 5]

[Figure 6]
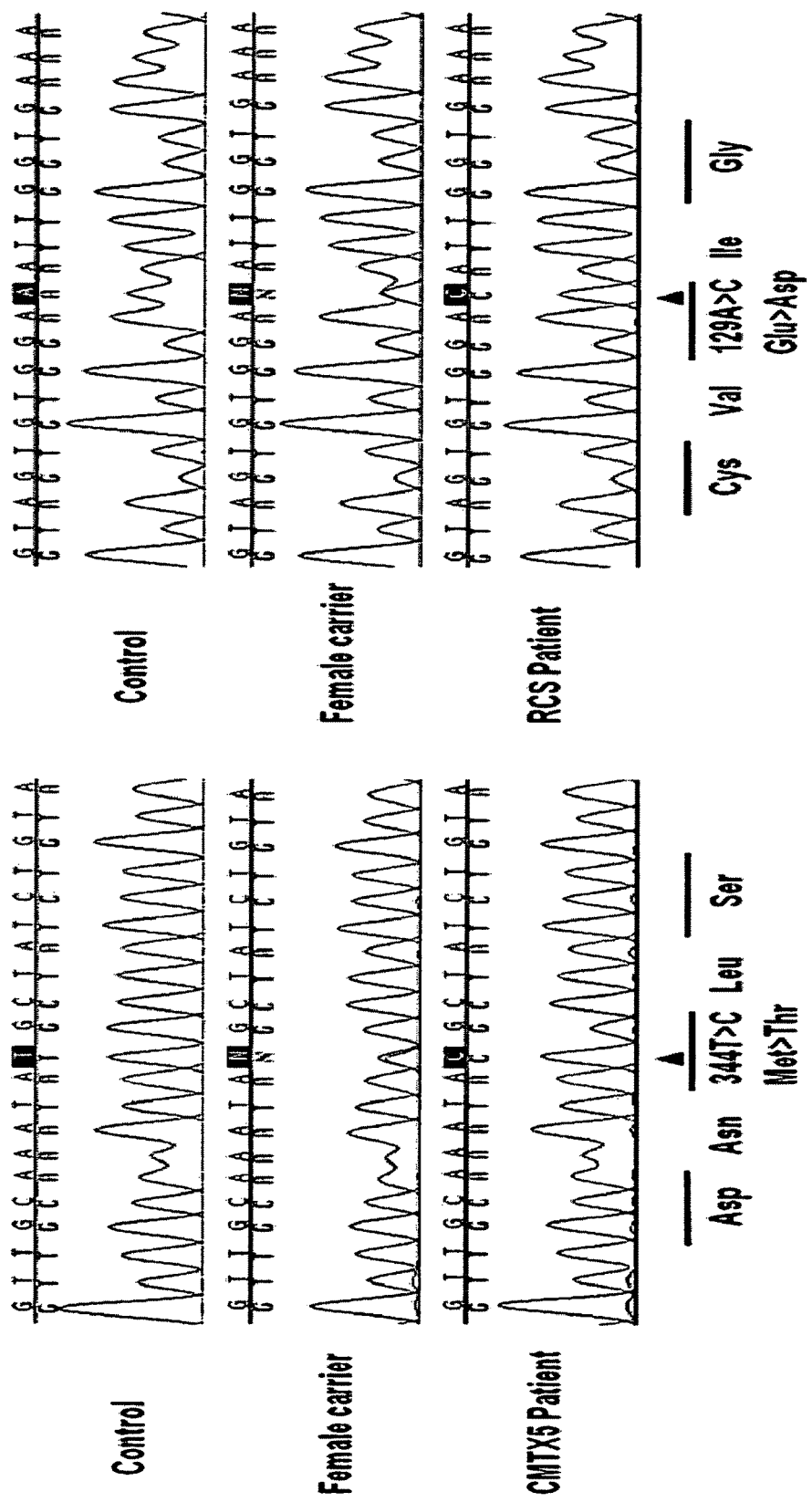

[Figure 7]

| | | aa 31–55 | | aa 103–127 |
|---|---|---|---|---|
| H. sapiens | NP_002755 | VTKKFSNQETCVELGESVRGEDVYI | | SRAPISAKLVANMLSVAGADHIITM |
| C. famillaris | XP_862484 | VTKKFSNQETCVELGESVRGEDVYI | | SRAPISAKLVANMLSVAGADHIITM (aa 111–135) |
| R. norvegicus | NP_058939 | VTKKFSNQETCVELGESVRGEDVYI | | SRAPISAKLVANMLSVAGADHIITM |
| M. musculus | NP_067438 | VTKKFSNQETCVELGESVRGEDVYI | | SRAPISAKLVANMLSVAGADHIITM |
| D. rerio | BC045301 | VTKKFSNQETCVELGESVRGEDVYI | | SRAPISAKLVANMLSVAGADHIITM |
| S. tropicalis | BC061401 | VTKKFSNQETCVELGESVRGEDVYI | | SRAPISAKLVANMLSVAGADHIITM |
| | | ************************* | | ************************* |

[Figure 8]

| SeqA Name | Len(aa) | SeqB Name | Len(aa) | Score |
|---|---|---|---|---|
| 1 Homo | 318 | 2 Canis | 326 | 100 |
| 1 Homo | 318 | 3 Rattus | 318 | 100 |
| 1 Homo | 318 | 4 Mus | 318 | 100 |
| 1 Homo | 318 | 5 Silurana | 318 | 96 |
| 1 Homo | 318 | 6 Danio | 318 | 96 |
| 2 Canis | 326 | 3 Rattus | 318 | 100 |
| 2 Canis | 326 | 4 Mus | 318 | 100 |
| 2 Canis | 326 | 5 Silurana | 318 | 96 |
| 2 Canis | 326 | 6 Danio | 318 | 96 |
| 3 Rattus | 318 | 4 Mus | 318 | 100 |
| 3 Rattus | 318 | 5 Silurana | 318 | 96 |
| 3 Rattus | 318 | 6 Danio | 318 | 96 |
| 4 Mus | 318 | 5 Silurana | 318 | 96 |
| 4 Mus | 318 | 6 Danio | 318 | 96 |
| 5 Silurana | 318 | 6 Danio | 318 | 95 |

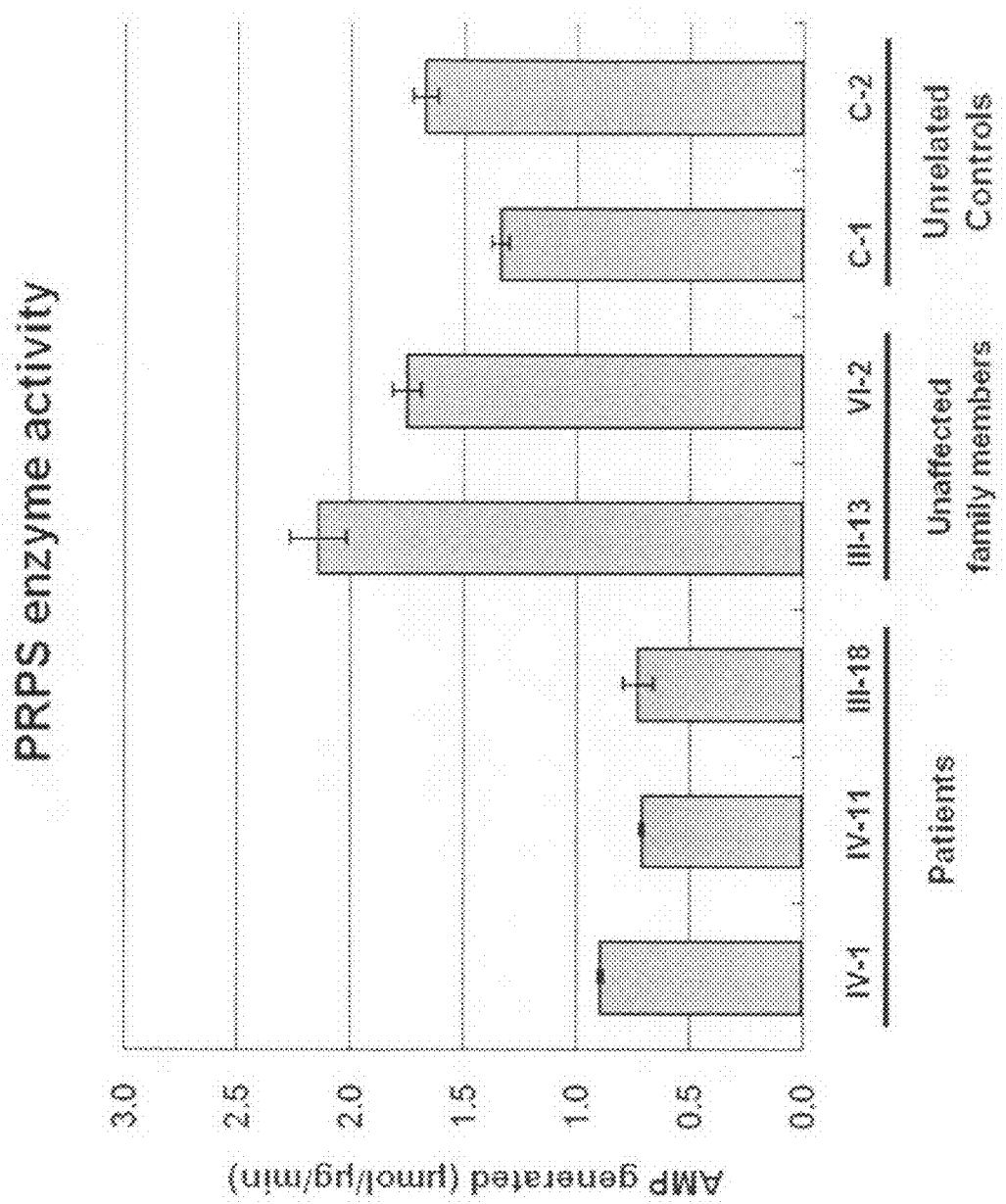
[Figure 9]

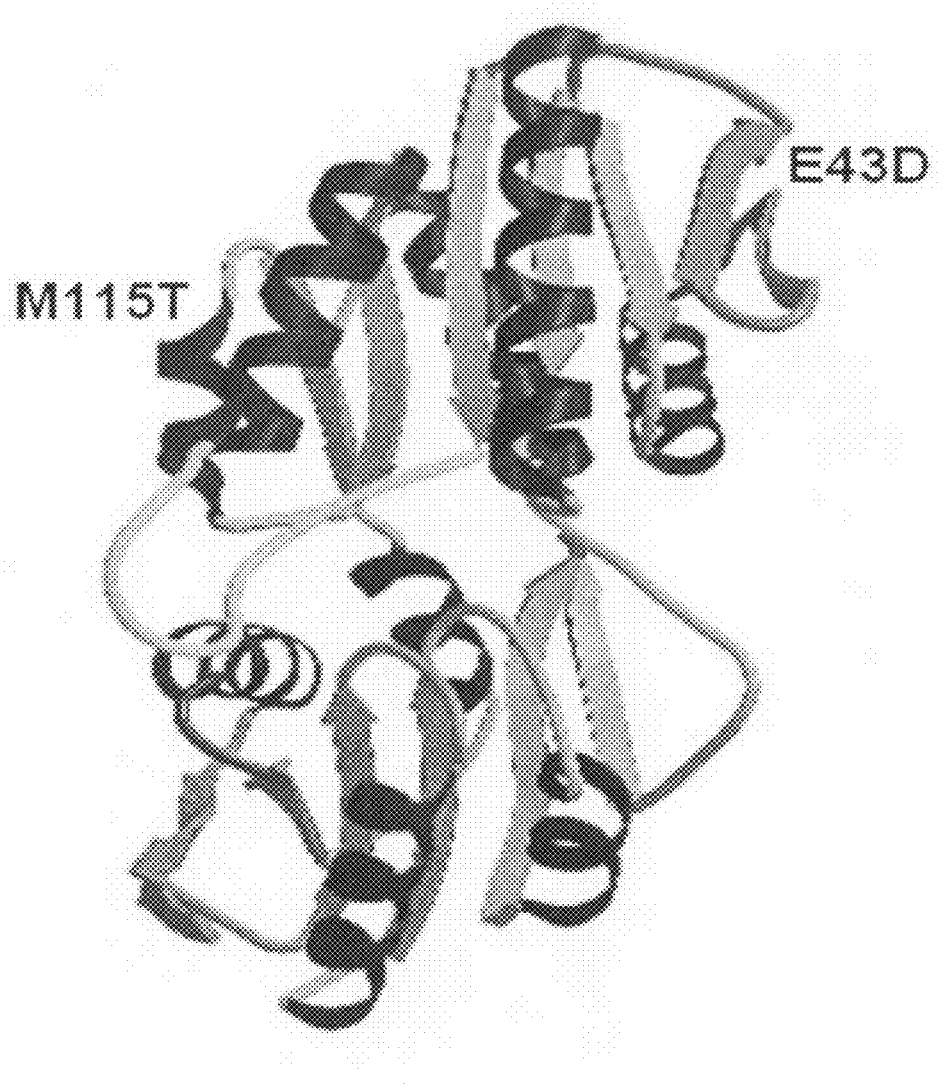
[Figure 10]

[Figure 11]
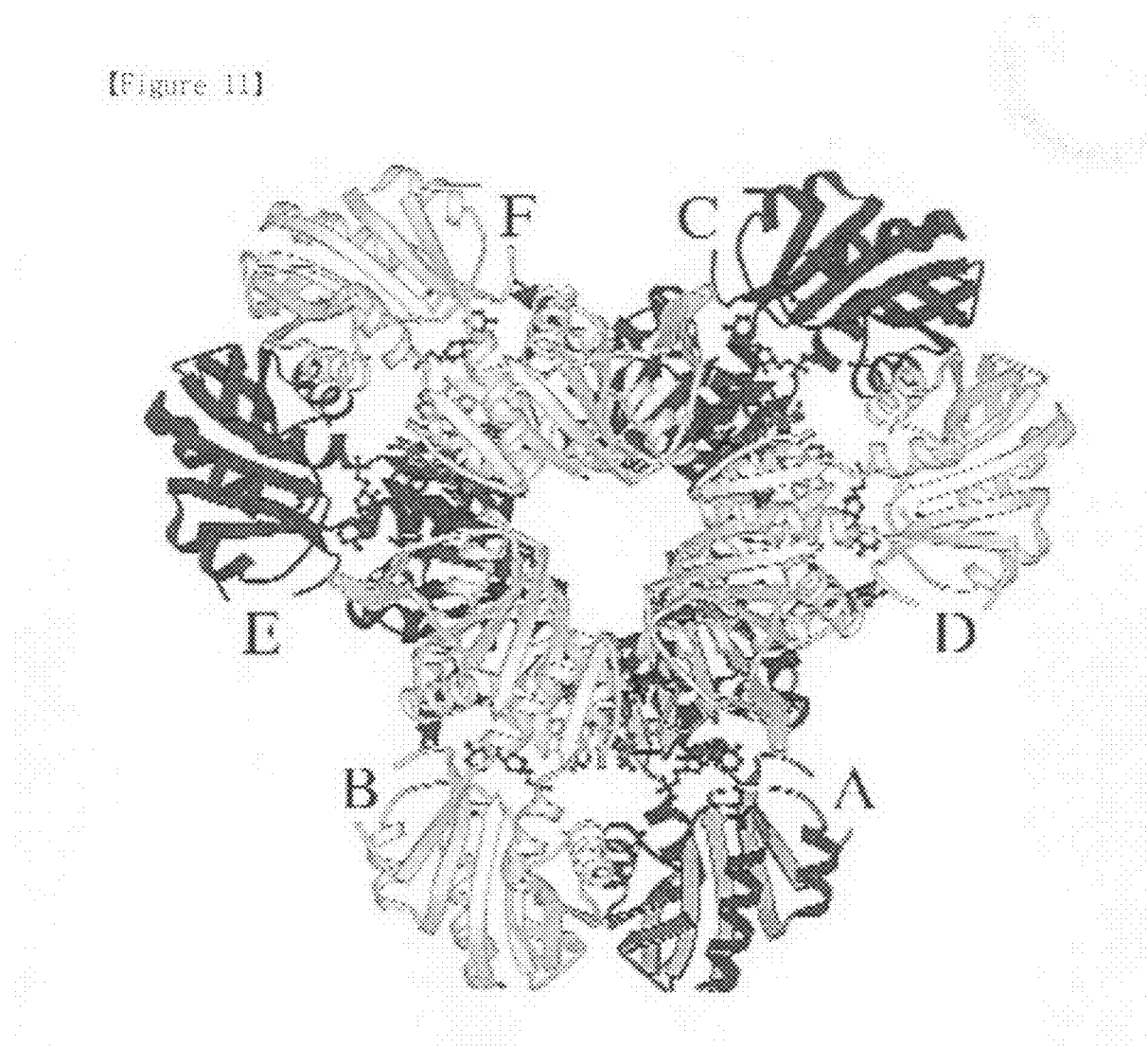

SEQUENCE LISTING

<160> NUMBER OF SEQ ID NOS: 18

<210> SEQ ID NO 1
<211> LENGTH: 2078
<212> TYPE: DNA
<213> ORGANISM: Homo sapiens

<400> SEQUENCE: 1

| | | | | | |
|---|---|---|---|---|---|
| gcaacgcaaa | gcgcttggta | ttgagtctgt | ggccgacttc | ggttccggtc | tctgcagcag | 60 |
| ccgtgatcgc | ttagtggagt | gcttagggta | gttggccagg | atgccgaata | tcaaaatctt | 120 |
| cagcggcagc | tcccaccagg | acttatctca | gaaaattgct | gaccgcctgg | gcctggagct | 180 |
| aggcaaggtg | gtgactaaga | aattcagcaa | ccaggagacc | tgtgtggaaa | ttggtgaaag | 240 |
| tgtacgtgga | gaggatgtct | acattgttca | gagtggttgt | ggcgaaatca | atgacaattt | 300 |
| aatggagctt | ttgatcatga | ttaatgcctg | caagattgct | tcagccagcc | gggttactgc | 360 |
| agtcatccca | tgcttccctt | atgcccggca | ggataagaaa | gataagagcc | gggcgccaat | 420 |
| ctcagccaag | cttgttgcaa | atatgctatc | tgtagcaggt | gcagatcata | ttatcaccat | 480 |
| ggacctacat | gcttctcaaa | ttcagggctt | ttttgatatc | ccagtagaca | atttgtatgc | 540 |
| agagccggct | gtcctaaagt | ggataaggga | gaatatctct | gagtggagga | actgcactat | 600 |
| tgtctcacct | gatgctggtg | gagctaagag | agtgacctcc | attgcagaca | ggctgaatgt | 660 |
| ggactttgcc | ttgattcaca | agaacggaa | gaaggccaat | gaagtggacc | gcatggtgct | 720 |
| tgtgggagat | gtgaaggatc | gggtggccat | ccttgtggat | gacatggctg | acacttgtgg | 780 |
| cacaatctgc | catgcagctg | acaaacttct | ctcagctggc | gccaccagag | tttatgccat | 840 |
| cttgactcat | ggaatcttct | ccggtcctgc | tatttctcgc | atcaacaacg | catgctttga | 900 |
| ggcagtagta | gtcaccaata | ccatacctca | ggaggacaag | atgaagcatt | gctccaaaat | 960 |
| acaggtgatt | gacatctcta | tgatccttgc | agaagccatc | aggagaactc | acaatggaga | 1020 |
| atccgtttct | tacctattca | gccatgtccc | tttataatag | agtaacttct | gaggcttttt | 1080 |
| gagaataaaa | tccaccccac | ccttgtttcc | ccttggtatt | tgatgacaaa | ttcagcagaa | 1140 |
| gacccggctt | gctccagtgt | agctttctac | atcccacatc | aggtatatta | gagcttatcc | 1200 |
| gaactgggga | aagacggatt | gagattaact | gctgggacct | cctacctgca | ttatctcatt | 1260 |
| ctggcttcct | tgataattct | gtgggccttg | cagctttaac | tatagctcag | ctgctgcaag | 1320 |
| atttcagact | tttgaggatg | ttgtgtgagg | gtgtttgact | gtgactgggg | aagctcagac | 1380 |
| tactttgtat | gtgaatgctt | cagggttttc | tttgttgaga | acaactagca | acaaaggcaa | 1440 |
| cccatgtgtg | accagttctc | cccaaggtct | atgctaaatt | atagcaagag | ccctgggcaa | 1500 |
| ccccaaaacct | agtcctggta | gctgagcacc | ctgtaaggca | ggagcaggca | gctcagcttg | 1560 |
| agcagacatt | gggtgggggg | tggggggtgg | ttgagggggg | aggcagcaca | gtgcagcaaa | 1620 |
| tgtttcttgg | gaggaagaag | cctgatccat | caccatctgc | ttgactatgt | agcttggatt | 1680 |
| ctcctttgta | cctatccctt | tcgatttggc | tttaccttca | tctatcttga | tccttttcctg | 1740 |
| gccaaatatc | ctcttgggcc | caaatgaaca | ttgtaccata | gtcttctgga | aagcaaacat | 1800 |
| gcttcctgct | atgtaattgc | taacattcat | attagatgat | gtgctgtagc | ttgatcttcc | 1860 |
| ttagcctact | gccactgagg | cagtaggttt | taggtggtat | cgtagtgcct | tttgattaat | 1920 |
| ttaagtattt | aattttcatc | ttccttcttt | ggatctattt | ggcctctcaa | atgaactgag | 1980 |
| attcctgtta | aaaagattg | atgttattgt | ctcttgtaga | ggaaactaat | aaagtgtgtg | 2040 |

-continued tacctgtgtg aaaaaaaaaa aaaaaaaaaa aaaaaaaa    2078

<210> SEQ ID NO 2
<211> LENGTH: 20
<212> TYPE: DNA
<213> ORGANISM: Artificial Sequence
<220> FEATURE:
<223> OTHER INFORMATION: PRPS1_e01F

<400> SEQUENCE: 2
ggaatgtaag atggcggagt    20

<210> SEQ ID NO 3
<211> LENGTH: 19
<212> TYPE: DNA
<213> ORGANISM: Artificial Sequence
<220> FEATURE:
<223> OTHER INFORMATION: PRPS1_e01R

<400> SEQUENCE: 3
acagagctgc accctctcc    19

<210> SEQ ID NO 4
<211> LENGTH: 23
<212> TYPE: DNA
<213> ORGANISM: Artificial Sequence
<220> FEATURE:
<223> OTHER INFORMATION: PRPS1_e02F

<400> SEQUENCE: 4
catgttcaat acaggtgcaa ttt    23

<210> SEQ ID NO 5
<211> LENGTH: 26
<212> TYPE: DNA
<213> ORGANISM: Artificial Sequence
<220> FEATURE:
<223> OTHER INFORMATION: PRPS1_e02R

<400> SEQUENCE: 5
gggtaatacc taagaaaagg tgattt    26

<210> SEQ ID NO 6
<211> LENGTH: 22
<212> TYPE: DNA
<213> ORGANISM: Artificial Sequence
<220> FEATURE:
<223> OTHER INFORMATION: PRPS1_e03F

<400> SEQUENCE: 6
ttctgggtac catagtgcct tt    22

<210> SEQ ID NO 7
<211> LENGTH: 21
<212> TYPE: DNA
<213> ORGANISM: Artificial Sequence
<220> FEATURE:
<223> OTHER INFORMATION: PRPS1_e03R

<400> SEQUENCE: 7
tgcctcccta tctaaccacc t    21

<210> SEQ ID NO 8
<211> LENGTH: 20
<212> TYPE: DNA
<213> ORGANISM: Artificial Sequence
<220> FEATURE:

<223> OTHER INFORMATION: PRPS1_e04F

<400> SEQUENCE: 8
ggctgggctc tctcacatag                                                    20

<210> SEQ ID NO 9
<211> LENGTH: 21
<212> TYPE: DNA
<213> ORGANISM: Artificial Sequence
<220> FEATURE:
<223> OTHER INFORMATION: PRPS1_e04R

<400> SEQUENCE: 9 aggaccccttt ttctgtcttg t                                                 21

<210> SEQ ID NO 10
<211> LENGTH: 22
<212> TYPE: DNA
<213> ORGANISM: Artificial Sequence
<220> FEATURE:
<223> OTHER INFORMATION: PRPS1_e05F

<400> SEQUENCE: 10
ctatctcctg accttgtgat cc                                                 22

<210> SEQ ID NO 11
<211> LENGTH: 23
<212> TYPE: DNA
<213> ORGANISM: Artificial Sequence
<220> FEATURE:
<223> OTHER INFORMATION: PRPS1_e05R

<400> SEQUENCE: 11
aagccttggg tgataaaaat ctc                                                23

<210> SEQ ID NO 12
<211> LENGTH: 20
<212> TYPE: DNA
<213> ORGANISM: Artificial Sequence
<220> FEATURE:
<223> OTHER INFORMATION: PRPS1_e06F

<400> SEQUENCE: 12
ggcctcagca tgacacctac                                                    20

<210> SEQ ID NO 13
<211> LENGTH: 23
<212> TYPE: DNA
<213> ORGANISM: Artificial Sequence
<220> FEATURE:
<223> OTHER INFORMATION: PRPS1_e06R

<400> SEQUENCE: 13
aaatccttca gaccaaagaa aga                                                23

<210> SEQ ID NO 14
<211> LENGTH: 20
<212> TYPE: DNA
<213> ORGANISM: Artificial Sequence
<220> FEATURE:
<223> OTHER INFORMATION: PRPS1_e07F

<400> SEQUENCE: 14
ccagccgtaa gtggctatct                                                    20

<210> SEQ ID NO 15

```
<211> LENGTH: 20
<212> TYPE: DNA
<213> ORGANISM: Artificial Sequence
<220> FEATURE:
<223> OTHER INFORMATION: PRPS1_e07R

<400> SEQUENCE: 15
aggtaggagg tcccagcagt                                                  20

<210> SEQ ID NO 16
<211> LENGTH: 318
<212> TYPE: PRT
<213> ORGANISM: Homo sapiens

<400> SEQUENCE: 16
```

Met Pro Asn Ile Lys Ile Phe Ser Gly Ser Ser His Gln Asp Leu Ser
 1               5                  10                  15

Gln Lys Ile Ala Asp Arg Leu Gly Leu Glu Leu Gly Lys Val Val Thr
            20                  25                  30

Lys Lys Phe Ser Asn Gln Glu Thr Cys Val Glu Ile Gly Glu Ser Val
        35                  40                  45

Arg Gly Glu Asp Val Tyr Ile Val Gln Ser Gly Cys Gly Glu Ile Asn
 50                  55                  60

Asp Asn Leu Met Glu Leu Leu Ile Met Ile Asn Ala Cys Lys Ile Ala
 65                  70                  75                  80

Ser Ala Ser Arg Val Thr Ala Val Ile Pro Cys Phe Pro Tyr Ala Arg
                85                  90                  95

Gln Asp Lys Lys Asp Lys Ser Arg Ala Pro Ile Ser Ala Lys Leu Val
            100                 105                 110

Ala Asn Met Leu Ser Val Ala Gly Ala Asp His Ile Ile Thr Met Asp
        115                 120                 125

Leu His Ala Ser Gln Ile Gln Gly Phe Phe Asp Ile Pro Val Asp Asn
130                 135                 140

Leu Tyr Ala Glu Pro Ala Val Leu Lys Trp Ile Arg Glu Asn Ile Ser
145                 150                 155                 160

Glu Trp Arg Asn Cys Thr Ile Val Ser Pro Asp Ala Gly Gly Ala Lys
                165                 170                 175

Arg Val Thr Ser Ile Ala Asp Arg Leu Asn Val Asp Phe Ala Leu Ile
            180                 185                 190

His Lys Glu Arg Lys Lys Ala Asn Glu Val Asp Arg Met Val Leu Val
        195                 200                 205

Gly Asp Val Lys Asp Arg Val Ala Ile Leu Val Asp Asp Met Ala Asp
210                 215                 220

Thr Cys Gly Thr Ile Cys His Ala Ala Asp Lys Leu Leu Ser Ala Gly
225                 230                 235                 240

Ala Thr Arg Val Tyr Ala Ile Leu Thr His Gly Ile Phe Ser Gly Pro
                245                 250                 255

Ala Ile Ser Arg Ile Asn Asn Ala Cys Phe Glu Ala Val Val Val Thr
            260                 265                 270

Asn Thr Ile Pro Gln Glu Asp Lys Met Lys His Cys Ser Lys Ile Gln
        275                 280                 285

Val Ile Asp Ile Ser Met Ile Leu Ala Glu Ala Ile Arg Arg Thr His
290                 295                 300

Asn Gly Glu Ser Val Ser Tyr Leu Phe Ser His Val Pro Leu
305                 310                 315

```
<210> SEQ ID NO 17
```

<211> LENGTH: 2078
<212> TYPE: DNA
<213> ORGANISM: Homo sapiens

<400> SEQUENCE: 17

| | | | | | |
|---|---|---|---|---|---|
| gcaacgcaaa | gcgcttggta | ttgagtctgt | ggccgacttc | ggttccggtc | tctgcagcag | 60 |
| ccgtgatcgc | ttagtggagt | gcttagggta | gttggccagg | atgccgaata | tcaaaatctt | 120 |
| cagcggcagc | tcccaccagg | acttatctca | gaaaattgct | gaccgcctgg | gcctggagct | 180 |
| aggcaaggtg | gtgactaaga | aattcagcaa | ccaggagacc | tgtgtggaaa | ttggtgaaag | 240 |
| tgtacgtgga | gaggatgtct | acattgttca | gagtggttgt | ggcgaaatca | atgacaattt | 300 |
| aatggagctt | ttgatcatga | ttaatgcctg | caagattgct | tcagccagcc | gggttactgc | 360 |
| agtcatccca | tgcttcccct | atgcccggca | ggataagaaa | gataagagcc | gggcgccaat | 420 |
| ctcagccaag | cttgttgcaa | atacgctatc | tgtagcaggt | gcagatcata | ttatcaccat | 480 |
| ggacctacat | gcttctcaaa | ttcagggctt | ttttgatatc | ccagtagaca | atttgtatgc | 540 |
| agagccggct | gtcctaaagt | ggataaggga | gaatatctct | gagtggagga | actgcactat | 600 |
| tgtctcacct | gatgctggtg | gagctaagag | agtgacctcc | attgcagaca | ggctgaatgt | 660 |
| ggactttgcc | ttgattcaca | agaacggaa | gaaggccaat | gaagtggacc | gcatggtgct | 720 |
| tgtgggagat | gtgaaggatc | gggtggccat | ccttgtggat | gacatggctg | acacttgtgg | 780 |
| cacaatctgc | catgcagctg | acaaacttct | ctcagctggc | gccaccagag | tttatgccat | 840 |
| cttgactcat | ggaatcttct | ccggtcctgc | tatttctcgc | atcaacaacg | catgctttga | 900 |
| ggcagtagta | gtcaccaata | ccatacctca | ggaggacaag | atgaagcatt | gctccaaaat | 960 |
| acaggtgatt | gacatctcta | tgatccttgc | agaagccatc | aggagaactc | acaatggaga | 1020 |
| atccgtttct | tacctattca | gccatgtccc | tttataatag | agtaacttct | gaggcttttt | 1080 |
| gagaataaaa | tccaccccac | ccttgtttcc | ccttggtatt | tgatgacaaa | ttcagcagaa | 1140 |
| gacccggctt | gctccagtgt | agctttctac | atcccacatc | aggtatatta | gagcttatcc | 1200 |
| gaactgggga | aagacggatt | gagattaact | gctgggacct | cctacctgca | ttatctcatt | 1260 |
| ctggcttcct | tgataattct | gtgggccttg | cagctttaac | tatagctcag | ctgctgcaag | 1320 |
| atttcagact | tttgaggatg | ttgtgtgagg | gtgtttgact | gtgactgggg | aagctcagac | 1380 |
| tactttgtat | gtgaatgctt | cagggttttc | tttgttgaga | acaactagca | acaaaggcaa | 1440 |
| cccatgtgtg | accagttctc | cccaaggtct | atgctaaatt | atagcaagag | ccctgggcaa | 1500 |
| ccccaaacct | agtcctggta | gctgagcacc | ctgtaaggca | ggagcaggca | gctcagcttg | 1560 |
| agcagacatt | gggtgggggg | tgggggtgg | ttgagggggg | aggcagcaca | gtgcagcaaa | 1620 |
| tgtttcttgg | gaggaagaag | cctgatccat | caccatctgc | ttgactatgt | agcttggatt | 1680 |
| ctcctttgta | cctatcccctt | tcgatttggc | tttaccttca | tctatcttga | tcctttcctg | 1740 |
| gccaaatatc | tcttgggcc | caaatgaaca | ttgtaccata | gtcttctgga | aagcaaacat | 1800 |
| gcttcctgct | atgtaattgc | taacattcat | attagatgat | gtgctgtagc | ttgatcttcc | 1860 |
| ttagcctact | gccactgagg | cagtaggttt | taggtggtat | cgtagtgcct | tttgattaat | 1920 |
| ttaagtattt | aattttcatc | ttccttcttt | ggatctattt | ggcctctcaa | atgaactgag | 1980 |
| attcctgtta | aaaagattg | atgttattgt | ctccttgtaga | ggaaactaat | aaagtgtgtg | 2040 |
| tacctgtgtg | aaaaaaaaaa | aaaaaaaaa | aaaaaaaa | | | 2078 |

<210> SEQ ID NO 18
<211> LENGTH: 318
<212> TYPE: PRT

-continued

<213> ORGANISM: Homo sapiens

<400> SEQUENCE: 18

```
Met Pro Asn Ile Lys Ile Phe Ser Gly Ser Ser His Gln Asp Leu Ser
  1               5                  10                  15
Gln Lys Ile Ala Asp Arg Leu Gly Leu Glu Leu Gly Lys Val Val Thr
                 20                  25                  30
Lys Lys Phe Ser Asn Gln Glu Thr Cys Val Glu Ile Gly Glu Ser Val
             35                  40                  45
Arg Gly Glu Asp Val Tyr Ile Val Gln Ser Gly Cys Gly Glu Ile Asn
         50                  55                  60
Asp Asn Leu Met Glu Leu Leu Ile Met Ile Asn Ala Cys Lys Ile Ala
 65                  70                  75                  80
Ser Ala Ser Arg Val Thr Ala Val Ile Pro Cys Phe Pro Tyr Ala Arg
                 85                  90                  95
Gln Asp Lys Lys Asp Lys Ser Arg Ala Pro Ile Ser Ala Lys Leu Val
            100                 105                 110
Ala Asn Thr Leu Ser Val Ala Gly Ala Asp His Ile Ile Thr Met Asp
            115                 120                 125
Leu His Ala Ser Gln Ile Gln Gly Phe Phe Asp Ile Pro Val Asp Asn
            130                 135                 140
Leu Tyr Ala Glu Pro Ala Val Leu Lys Trp Ile Arg Glu Asn Ile Ser
145                 150                 155                 160
Glu Trp Arg Asn Cys Thr Ile Val Ser Pro Asp Ala Gly Gly Ala Lys
                165                 170                 175
Arg Val Thr Ser Ile Ala Asp Arg Leu Asn Val Asp Phe Ala Leu Ile
                180                 185                 190
His Lys Glu Arg Lys Lys Ala Asn Glu Val Asp Arg Met Val Leu Val
            195                 200                 205
Gly Asp Val Lys Asp Arg Val Ala Ile Leu Val Asp Asp Met Ala Asp
        210                 215                 220
Thr Cys Gly Thr Ile Cys His Ala Ala Asp Lys Leu Leu Ser Ala Gly
225                 230                 235                 240
Ala Thr Arg Val Tyr Ala Ile Leu Thr His Gly Ile Phe Ser Gly Pro
                245                 250                 255
Ala Ile Ser Arg Ile Asn Asn Ala Cys Phe Glu Ala Val Val Val Thr
            260                 265                 270
Asn Thr Ile Pro Gln Glu Asp Lys Met Lys His Cys Ser Lys Ile Gln
            275                 280                 285
Val Ile Asp Ile Ser Met Ile Leu Ala Glu Ala Ile Arg Arg Thr His
        290                 295                 300
Asn Gly Glu Ser Val Ser Tyr Leu Phe Ser His Val Pro Leu
305                 310                 315
```

MUTATION OF PRPS1 GENE CAUSING CMTX5 DISEASE AND THE USE THEREOF

TECHNICAL FIELD

The present invention relates to a PRPS1 gene mutation associated with acquired peripheral neuropathy resulting from a decrease in the activity of a metabolic enzyme critical for purine metabolism and nucleotide biosynthesis, and to the use thereof.

BACKGROUND ART

The present invention relates to a missense-mutated protein at conserved amino acids in the PRPS1 (phosphoribosyl pyrophosphate synthetase 1) gene on Xq22.3 in two families with a syndromic form of inherited peripheral neuropathy, one of Asian and one of European descent, and to a mutation of the gene.

Charcot-Marie-Tooth (CMT) inherited neuropathy (CMT) represents a clinically and genetically heterogeneous group of hereditary peripheral neuropathies characterized by chronic motor and sensory impairment. It is one of the most common inherited disorders of humans and is the most common genetic cause of neuropathy, with prevalence of 1 in 2500 people [see Skre H (1974) Genetic and clinical aspects of Charcot-Marie-Tooth's disease. Clin Genet 6:98-118]. Also, about 10-20% of CMT is inherited in an X-linked manner (CMTX). Male patients with this disease gene invariably develop sensorineural hearing loss of prelingual type followed by gating disturbance and visual loss. The family of European descent was reported in 1967 as having Rosenberg-Chutorian syndrome, and recently a Korean family with the same symptom triad was identified with a novel disease locus CMTX5 on the chromosome band Xq21.32-q24. Meanwhile, it was reported that patients suffering from RCS did not show mental retardation, like the case of CMTX5 [see Rosenberg R N, Chutorian A (1967) Familial opticoacoustic nerve degeneration and polyneuropathy. Neurology 17:827-832].

Among the five known loci for CMTX, the causal gene has been identified only in CMTX1 (MIM 302800), in which the neuropathy is caused by mutations in the gap junction protein beta 1 gene (GJB1 [MIM 304040) encoding the protein connexin 32 (Cx32) [see Bergoffen J, Scherer S S, Wang S, Scott M O, Bone L J, Paul D L, Chen K, Lensch M W, Chance P F, Fischbeck K H (1993) Connexin mutations in X-linked Charcot-Marie-Tooth disease. Science 262:2039-2042]. A syndromic form of X-linked recessive CMT was identified in a Korean family, and the disease gene was localized to a novel locus for CMTX on the chromosome band Xq21.32-24 (CMTX5 [MIM 311070) [see Kim H J, Hong S H, Ki C S, Kim B J, Shim J S, Cho S H, Park J H, Kim J W (2005) A novel locus for X-linked recessive CMT with deafness and optic neuropathy maps to Xq21.32-q24. Neurology 64:1964-1967].

Meanwhile, in the present invention, the male patients with CMTX5 invariably developed a unique symptom triad of hearing loss, visual impairment, and peripheral neuropathy (see Table 1 and FIG. 1). The hearing loss is characterized as sensorineural and prelingual in nature. The patients experienced progressive visual impairment from optic neuropathy at about 10 years of age. At approximately the same age, the patients also experienced peripheral neuropathy that has been classified by electrophysiology as having mixed features of segmental demyelination and axonal loss. Follow-up of the youngest male patient (CMTX5:IV-11 in FIG. 1), who had been reported to have normal visual function at the time of initial presentation (at age 4 years), showed that his visual function began to be impaired at age 7 years. Pathologic examination of the sural nerve biopsy sample from the eldest living patient (CMTX5:III-18 in FIG. 1) showed loss of both large and small myelinated nerve fibers and an increase of endoneurial collagen (FIG. 3). Electron microscopic examination revealed segmental demyelination and remyelination with onion-bulb formation (FIG. 4). The three symptoms observed in CMTX5 were identical with that reported in Rosenberg-Chutorian syndrome (RCS) (Table 1 and FIG. 2), and it has been speculated that CMTX5 and RCS are allelic disorders sharing the common disease gene.

TABLE 1

Characteristics of patients with CMTX5 and RCS, a disease allelic to CMTX5

| Patient | Age (y)[a]/sex | Hearing loss (Age at onset, y) | Visual impairment (Age at onset, y) | Motor (Age at onset, y) | Distal sensory loss | MNCV of median nerve (m s$^{-1}$) | Uric acid level[b] (age[c], y) |
|---|---|---|---|---|---|---|---|
| CMTX5:III-18 | 28/male | +(Since infant) | +(11) | +(12) | + | NT | 4.48 (29) |
| CMTX5:III-21 | 25/male | +(Since infant) | +(13) | +(12) | − | NT | NT |
| CMTX5:III-24 | 18/male | +(Since infant) | +(8) | +(12) | − | NT | NT |
| CMTX5:IV-1 | 14/male | +(Since infant) | +(11) | +(10) | − | 51.0 | 3.36 (14) |
| CMTX5:IV-11 | 4/male | +(Since infant) | +(7)[d] | +(4) | − | 43.1 | 4.73 (5) |
| RCS:III-11 | 32/male | +(Since infant) | +(20) | +(5) | + | 44.8 | 5.43 (70) |
| RCS:III-13 | 29/male | +(Since infant) | +(19) | +(2) | + | 46.5 | 3.53 (68) |
| RCS:IV-14 | 3.5/male | +(Since infant) | − | Nonspecific | − | NT | NT |

Note:
RCS = Rosenberg-Chutorian syndrome;
MNCV = motor nerve conduction velocity;
NT = Not tested.
[a]Age at initial clinical evaluation and electrophysiological studies.
[b]+ = positive finding; − = negative finding.
[c]Reference range, 3.40-7.20 mg/dL.
[d]Age at the time of blood drawing for the determination of uric acid levels.
[e]Follow-up examination of this patient (IV-11) showed decreased visual acuity 3 years after the initial evaluation (at age 7 years).

The present inventors have found that the disease locus of CMTX5 spans 15.2 cM and harbors more than 170 known genes and predicted genes. Accordingly, the present inventors have investigated the candidate genes that were known to be expressed in the inner ear according to the cochlear expression database (Morton cochlear expression database) within the locus, since sensorineural hearing loss has been the earliest symptom and sign of both CMTX5 and RCS [see Resendes B L, Robertson N G, Szustakowski J D, Resendes R J, Weng Z, Morton C C (2002) Gene discovery in the auditory system: characterization of additional cochlear-expressed sequences. J Assoc Res Otolaryngol 3:45-53].

Mutations identified in the present invention were E43D, in patients with Rosenberg-Chutorian syndrome, and M115T, in the Korean patients with CMTX5 (see SEQ ID NOs: 16 and 18). Also, enzyme activity decreased in patients with M115T.

Meanwhile, previous reports of missense mutations in PRPS1 have demonstrated increased rather than decreased enzyme activity, with "superactive" enzymes resulting in hyperuricemia and gout (MIM 311850) [see Becker M A, Smith P R, Taylor W, Mustafi R, Switzer R L (1995) The genetic and functional basis of purine nucleotide feedback-resistant phosphoribosylpyrophosphate synthetase superactivity. J Clin Invest 96:2133-2141; and Becker M A, Taylor W, Smith P R, Ahmed M (1996) Overexpression of the normal phosphoribosylpyrophosphate synthetase 1 isoform underlies catalytic superactivity of human phosphoribosylpyrophosphate synthetase. J Biol Chem 271:19894-19899]. Also, it was reported that such mutations also caused sensorineural hearing loss and developmental delay [see Simmonds H A, Webster D R, Lingam S, Wilson J (1985), An inborn error of purine metabolism, deafness and neurodevelopmental abnormality. Neuropediatrics 16:106-108].

However, in the present invention, all serum uric acid levels in patients with CMTX5 and RCS were shown to have normal values (Table 1). No patient with CMTX5 or RCS had been diagnosed with gout or had other hyperuricemia-related symptoms or signs. These results demonstrate that the mutated PRPS1 of the present invention shows a decreased enzymatic activity, but can damage the nervous system without elevating uric acid levels. Accordingly, the use of a screening system with the mutated PRPS1 protein of the present invention allows the screening of drug candidates which increase or decrease the activity of PRPS1. The development of this screening system can be performed using a prior method for screening protein drugs.

Also, a kit, containing the mutated PRPS1 protein and a mutated gene thereof, can be used to diagnose acquired peripheral neuropathy. The kit can be prepared using any method known in the art.

The functional form of the PRPS1 enzyme was shown to have a hexameric structure. The PRPS1 monomer has five-stranded parallel β sheets and four α-helices on each of the N- and C-terminal domains, flanked by a short antiparallel β sheet protruding from the central core (a "flag" region) [see Eriksen T A, Kadziola A, Bentsen A K, Harlow K W, Larsen S (2000) Structural basis for the function of *Bacillus subtilis* phosphoribosyl-pyrophosphate synthetase. Nat Struct Biol 7:303-308].

In addition to catalytic and regulatory binding sites, PRPS1 has functional residues involved in intersubunit interactions and maintaining the stability of the enzyme. The mutation in CMTX5 occurred at the Met 115 residue of α-helix of N-terminal domain, and the mutation in RCS occurred at the Glu 43 residue of the "flag" region of the N-terminal domain (FIG. 10) [see Eriksen T A, Kadziola A, Bentsen A K, Harlow K W, Larsen S (2000) Structural basis for the function of *Bacillus subtilis* phosphoribosyl-pyrophosphate synthetase. Nat Struct Biol 7:303-308]. It was speculated that the increased enzyme activity was caused by mutations that alter the transmission of allosteric effects on the active sites of PRPS1, resulting in decreased inhibition [see Becker M A, Smith P R, Taylor W, Mustafi R, Switzer R L (1995) The genetic and functional basis of purine nucleotide feedback-resistant phosphoribosylpyrophosphate synthetase superactivity. J Clin Invest 96:2133-2141].

In the present invention, the PRPS1 mutations causing decreased enzyme activity (CMTX5 and RCS) were occurring in the interface between the A and D subunits, whereas those causing increased enzyme activity were found in the interface between the A and C subunits, indicating that the different regulatory behaviors of mutations result from altered interactions between subunits (FIG. 11) [see Eriksen T A, Kadziola A, Bentsen A K, Harlow K W, Larsen S (2000) Structural basis for the function of *Bacillus subtilis* phosphoribosyl-pyrophosphate synthetase. Nat Struct Biol 7:303-308].

Meanwhile, acquired peripheral neuropathy, which can result from antimetabolite medications, is one of the major side effects of cancer chemotherapy and of other medications, such as statins and nucleoside reverse transcriptase inhibitors utilized to treat patients with HIV (drug-/chemotherapy-induced peripheral neuropathy) [see Peltier A C, Russell J W (2006) Advances in understanding drug-induced neuropathies. Drug Saf 29:23-30 and Sul J K, Deangelis L M (2006) Neurologic complications of cancer chemotherapy. Semin Oncol 33:324-332]. Some of these medications also cause sensorineural hearing loss and optic neuropathy, as in the patients with CMTX5 and RCS. Several agents have been developed for potential use as chemoprotectants to reduce these side effects, but none have proven effective [see Hausheer F H, Schilsky R L, Bain S, Berghorn E J, Lieberman F (2006) Diagnosis, management, and evaluation of chemotherapy-induced peripheral neuropathy. Semin Oncol 33:15-49].

Accordingly, the PRPS1 gene of the present invention is a metabolic enzyme critical for nucleotide biosynthesis, contributes to the pathophysiology of acquired peripheral neuropathy, and can be used as a therapeutic target to prevent or treat medication-induced acquired peripheral neuropathy, sensorineural hearing loss, and/or optic neuropathy [see Hausheer F H, Schilsky R L, Bain S, Berghorn E J, Lieberman F (2006) Diagnosis, management, and evaluation of chemotherapy-induced peripheral neuropathy. Semin Oncol 33:15-49 and Brinkman R R, Dube M P, Rouleau G A, Orr A C, Samuels M E (2006) Human monogenic disorders—a source of novel drug targets. Nat Rev Genet 7:249-260].

As described above, the present invention relates to the fact that missense mutations in the PRPS1 gene cause a syndromic form of peripheral neuropathy associated with sensorineural hearing loss and optic neuropathy. Accordingly, the present invention relates to inherited peripheral neuropathy resulting from decreased activity of a metabolic enzyme critical for purine metabolism and nucleotide biosynthesis, and relates to the understanding of peripheral nerve-specific metabolism and the treatment of antimetabolite-induced acquired peripheral neuropathy.

DISCLOSURE

Technical Problem

It is an object of the present invention to provide a gene mutation associated with inherited peripheral neuropathy.

Another object of the present invention is to provide a polypeptide which hybridizes specifically either with a polynucleotide comprising said mutation or with a complementary polynucleotide thereof.

Still another object of the present invention is to provide a polypeptide which is encoded by said polypeptide.

Still another object of the present invention is to provide an antibody which binds specifically to said polypeptide.

Still another object of the present invention is to provide a microarray chip for detecting said mutation, which comprises said polynucleotide.

Still another object of the present invention is to provide a method for diagnosing peripheral neuropathy associated with sensorineural hearing loss and optic neuropathy.

Yet another object of the present invention is to provide a method for detecting a mutation in a nucleic acid molecule.

Further still another object of the present invention is to provide a method for screening drugs for treating peripheral neuropathy associated with sensorineural hearing loss and optic neuropathy.

Technical Solution

To achieve the above objects, according to one aspect of the present invention, there is provided a polynucleotide, which comprises a mutated base of a polynucleotide of SEQ ID NO: 17 and consists of at least 10 consecutive nucleotides, or a complementary polynucleotide thereof.

According to another aspect of the present invention, there is provided a polynucleotide, which hybridizes specifically with said polynucleotide or a polynucleotide complementary thereto.

According to still another aspect of the present invention, there is provided a polypeptide which is encoded by said polynucleotide.

According to still another aspect of the present invention, there is provided an antibody which binds specifically to said polypeptide.

According to still another aspect of the present invention, there is provided a microarray chip for detecting mutations, which comprises said polynucleotide, a polypeptide which is encoded thereby, or a cDNA thereof.

According to still another aspect of the present invention, there is provided a kit for detecting mutations, which comprises said polynucleotide, a polypeptide which is encoded thereby, or a cDNA thereof.

According to still another aspect of the present invention, there is provided a method for identifying a subject having the risk of peripheral neuropathy associated with sensorineural hearing loss and optic neuropathy, the method comprising the steps of: isolating a nucleic acid sample; and ii) determining the location of a mutation in a polynucleotide of SEQ ID NO: 17.

According to still another aspect of the present invention, there is provided a method for detecting a mutation in a nucleic acid molecule, the method comprising the steps of: i) bringing a regent, which hybridizes specifically either with a polynucleotide comprising a mutated base in a polynucleotide SEQ ID NO: 17 and consisting of at least 10 consecutive nucleotides, or with a complementary polynucleotide thereof, in strict hybridization conditions, into contact with a test sample; and ii) detecting the formation of a hybridized double strand.

According to another aspect of the present invention, there is provided a method for screening drugs for treating peripheral neuropathy associated with sensorineural hearing loss and optic neuropathy, the method comprising the steps of: i) bringing a polypeptide, which is encoded either by a polynucleotide comprising a mutated base in a polynucleotide SEQ ID NO: 17 and consisting of at least 10 consecutive nucleotides, or with a complementary polynucleotide thereof, into contact with a candidate substance in conditions suitable for the formation of a bound complex.

Advantageous Effects

In the present invention, it was found that the mutated PRPS1 protein is a metabolic enzyme critical for purine metabolism and nucleotide biosynthesis. The decreased activity of the enzyme can cause acquired peripheral neuropathy, and thus the mutated PRPS1 protein according to the present invention can be used for the diagnosis and treatment of acquired peripheral neuropathy.

BRIEF DESCRIPTION OF THE DRAWINGS

The foregoing and other objects, features and advantages of the present invention will become more apparent from the following detailed description when taken in conjunction with the accompanying drawings in which:

FIGS. 1 and 2 show pedigrees of the Korean family with CMTX5 (FIG. 1) and the family of European descent with Rosenberg-Chutorian syndrome (RCS) (FIG. 2). Affected male patients are indicated by blackened boxes and the obligate carrier females by circles with central dots. The individuals whose blood was drawn for the present invention are marked with asterisks (*).

FIGS. 3 and 4 show sural nerve biopsy findings of a patient with CMTX5 (FIG. 3) and histological examination of the sural nerve biopsy sample (FIG. 4). The histological examination of the sural nerve biopsy sample revealed loss of myelinated nerve fibers and interstitial fibrosis (Luxol-fast blue, x400). Electron micrograph of the sural nerve showed myelinated axons surrounded by concentrically arranged cytoplasmic processes of Schwann cells forming an onion bulb. The arrow indicates a remyelinating axon with an abnormally thin myelin sheath.

FIG. 5 shows a transcript map of the region on chromosome band Xq22.3 within the CMTX5 locus and the genomic structure of PRPS1 with seven coding exons. Black bars represent coding sequences, and gray bars represent UTRs. All seven coding exons of PRPS1 were amplified and directly sequenced, according to standard procedures. The patients with CMTX5 had a missense mutation in exon 3 (blue circle), and the patients with RCS had a missense mutation in exon 2 (red circle).

FIG. 6 shows chromatograms of PRPS1 mutations detected by direct sequencing. M115T in patients with CMTX5 (left panel) and E43D in patients with RCS (right panel).

FIG. 7 shows that the affected amino acids are perfectly conserved across different species.

FIG. 8 shows multiple sequence alignment of PRPS1 by ClustalW, showing the degree of conservation of the amino acid sequences of the PRPS1 protein across different species. *Homo*=*Homo sapiens*; *Canis*=*Canis familiaris*; *Rattus*=*Rattus norvegicus*; *Mus*=*Mus musculus*; *Danio*=*Danio rerio*; and *Silurana*=*Silurana tropicalis*.

FIG. 9 shows PRPS enzyme activity, determined by measuring the degree of generation of AMP, the end product of PRPS enzyme, in cultured fibroblasts. The activity was decreased in patients with CMTX5 (CMTX5:IV-1, IV-11, and III-18) compared with unaffected family members and unrelated control individuals (CMTX5:III-13, VI-2 and C-1, C-2).

FIG. 10 shows the locations of the mutations on the ribbon diagram of the PRPS1 monomer. M115T in CMTX5 on the α-helix of N-terminal domain (blue) and E43D in RCS on the "flag" region of the N-terminal domain (green).

FIG. 11 shows hexameric structure and subunits of PRPS1.

MODE FOR INVENTION

Hereinafter, the present invention will be described in further detail with reference to non-limiting examples. It is to be understood, however, that these examples are not to be construed to limit the scope of the present invention. The literature cited in the present invention is incorporated herein by reference.

EXAMPLES

Example 1

Screening of PRPS1 Gene and Identification of Mutation

The study in the present invention was approved by the Institutional Review Board of the Samsung Medical Center, and written informed consent was obtained from all adult subjects and from parents on behalf of their children. Blood samples were collected and genomic DNA was isolated from peripheral blood leukocytes by the use of the Wizard genomic DNA purification kit, according to the manufacturer's instructions (Promega). All coding exons and their flanking intronic sequences of the candidate genes were amplified by PCR using the primers (SEQ ID NO: 2 to SEQ ID NO: 15) designed by the present inventors with the Primer3 program. Cycle sequencing was performed with the BigDye Terminator Cycle Sequencing Ready Reaction kit (Applied Biosystems) on the ABI 3100 Genetic Analyzer (Applied Biosystems). In the course of screening the genes expressed in the inner ear, the present inventors identified a 344T→C transition mutation (SEQ ID NO: 1 (NM_002764) and SEQ ID NO: 17, in which A of the first codon ATG encoding an amino acid residue as a translation initiation site is +1, and the $344^{th}$ base from the base A is a T-to-C substitution) in exon 3 of the phosphoribosyl pyrophosphate synthetase gene (PRPS1 [MIM 311850]) (FIGS. 5 and 6).

This sequence variation was not observed in 1,045 unrelated control chromosomes of Korean origin. On the basis of the hypothesis that the disease-causing gene would be same in CMTX5 and RCS, the present inventors obtained DNA samples from patients and family members with RCS. Direct sequencing analyses of the PRPS1 gene revealed a 129A→C transversion mutation in exon 2 of PRPS1 giving rise to E43D in the two clinically affected patients with RCS and confirmed the X-linked recessive inheritance in the family (FIG. 6). Also, the present inventors confirmed that E43D was not observed in 1,103 unrelated control chromosomes of Korean origin. The present inventors also performed direct sequencing of exon 2 and exon 3 of PRPS1 on DNA samples from 50 unrelated individuals of white origin (Coriell Cell Repositories catalogue ID HD50CAU) and confirmed that no sequence variations were observed. The primer sequences for the PRPS1 gene are available on request. The mutated amino acids in the Korean patients with CMTX5 and the patients with RCS both showed perfect conservation from zebrafish to human (FIG. 7). (Gene Accession No.: NM_002764).

Example 2

Examination of Frequency of PRPS1 Mutations in CMT Disease

To further examine the frequency of PRPS1 mutations in CMT, the present inventors performed direct sequencing of all coding exons and exon-intron boundary sequences of PRPS1 in 101 patients with CMT whose previous genetic test results had ruled out CMT1A (MIM 118220), the most common subtype of CMT (57 male patients and 44 female patients). As a result, the present inventors observed a single patient with a sequence variation in exon 4 (420G→A), which was considered to be a rare synonymous polymorphism (P140P) on the basis of our further observation of its occurrence in control chromosomes (1.1%; 2/185), and no patient had a mutation that altered the amino acid sequence of PRPS1. This indicates that PRPS1 is specifically mutated in CMTX5, causing the unique symptom triad, and that the gene is highly conserved even within the human species.

Example 3

Evaluation of Function of PRPS1 Mutant

To evaluate the function of the mutation, the present inventors determined the PRPS1 enzyme activity from fibroblasts obtained from skin biopsy samples from three patients with CMTX5 (CMTX5:IV-1, IV-11, and III-18), two nonaffected individuals in the CMTX5 family (CMTX5:III-13 and IV-2), and two unrelated adult control individuals (C-1 and C-2). Then, the PRPS activity was determined. For this purpose, 100 µl of cell extract (obtained from patients in the Samsung Medical Center during a period ranging from January, 2004 to December, 2007) was incubated for 60 min at 37° C., with 100 µl of a pH 7.4 reaction mixture containing: TrisHCl 50 mM, $MgCl_2$ 5 mM, EDTA 1 mM, DTT 1 mM, NaPi 32 mM, saturating concentrations of the substrates ATP (0.5 mM) and ribose 5-phosphate (0.15 mM), and $P^1 P^5$ diadenosine pentaphosphate (Ap5A, an inhibitor of adenylate kinase, 0.25 mM). On completion of the incubation, the reaction was stopped by heating at 70° C., and samples were centrifuged in Amicon cones (30,000 MW, Centricon™30, Millipore, Mass.). To determine the level of AMP generated from ATP, the filtrate was injected into a high-performance liquid chromatography (HPLC) system equipped with the Waters pre-packed µBondapak $C_{18}$ 10-µm column and was eluted at room temperature with 20 mM phosphate buffer (pH 2.5) at a flow rate of 1 ml/min. Nucleotide peaks were identified by coinjection with 25 µM AMP and GMP as standard. The instrument for HPLC and ultraviolet spectroscopy was the Waters Breeze HPLC system, and all reagents were obtained form Sigma-Aldrich. As a result, the present inventors observed that the mutation causing CMTX5 results in a partial loss of normal function, because the present inventors found decreased PRPS enzyme activity in patients compared with unaffected family members (i.e., those without the mutation) and unrelated control individuals (FIG. 9).

INDUSTRIAL APPLICABILITY

As can be seen from the foregoing, in the present invention, it was found that the mutated PRPS1 protein is a metabolic enzyme critical for purine metabolism and nucleotide biosynthesis. The decreased activity of the enzyme can cause acquired peripheral neuropathy, and thus the mutated PRPS1 protein can be used for the diagnosis and treatment of acquired peripheral neuropathy.

The invention claimed is:

1. An isolated PRPS1 (phosphoribosyl pyrophosphate synthetase 1) mutant gene having a nucleotide sequence of SEQ ID NO: 17.

2. An isolated polynucleotide encoding a polypeptide consisting of the amino acid sequence of SEQ ID NO: 18.

* * * * *